United States Patent [19]

Jahn et al.

[11] Patent Number: 4,936,906
[45] Date of Patent: * Jun. 26, 1990

[54] AGENTS FOR REGULATING PLANT GROWTH

[75] Inventors: Dieter Jahn, Edingen-Neckarhausen; Michael Keil, Freinsheim; Dieter Kolassa, Ludwigshafen; Ulrich Schirmer, Heidelberg; Rainer Becker, Bad Durkheim; Johann Jung; Wilhelm Rademacher, both of Limburgerhof, all of Fed. Rep. of Germany

[73] Assignee: BASF Aktiengesellschaft, Fed. Rep. of Germany

[*] Notice: The portion of the term of this patent subsequent to Oct. 25, 2005 has been disclaimed.

[21] Appl. No.: 881,385

[22] Filed: Jul. 2, 1986

[30] Foreign Application Priority Data

Jul. 4, 1985 [DE] Fed. Rep. of Germany ....... 3523862

[51] Int. Cl.$^5$ ............... A01N 37/34; A01N 37/06; A01N 37/08; A01N 31/04
[52] U.S. Cl. ........................ 71/105; 71/106; 71/107; 71/113; 71/115; 71/122; 558/430; 558/431; 560/124; 560/125; 560/126; 562/506; 562/507; 562/508; 568/376; 568/377
[58] Field of Search ............ 558/430, 431; 71/105, 71/106, 113, 122, 107, 115; 560/126; 562/508; 568/377

[56] References Cited

U.S. PATENT DOCUMENTS

| | | | |
|---|---|---|---|
| 4,075,239 | 2/1978 | Sawaki et al. | 558/431 |
| 4,515,729 | 5/1985 | Iwataki et al. | 558/431 |
| 4,517,013 | 5/1985 | Becker et al. | 558/431 X |
| 4,560,403 | 12/1985 | Motojima et al. | 71/106 |
| 4,584,013 | 4/1986 | Brunner | 71/94 |
| 4,693,745 | 9/1987 | Brunner | 562/508 X |
| 4,780,129 | 10/1988 | Becker et al. | 71/105 X |

FOREIGN PATENT DOCUMENTS

| | | |
|---|---|---|
| 123001 | 10/1984 | European Pat. Off. |
| 0046943 | 3/1982 | Japan ............... 558/431 |
| 0077848 | 5/1983 | Japan ............... 558/431 |

Primary Examiner—Joseph P. Brust
Attorney, Agent, or Firm—Keil & Weinkauf

[57] ABSTRACT

Agents for regulating plant growth containing an effective amount of at least one cyclohexanone derivative of the formula I

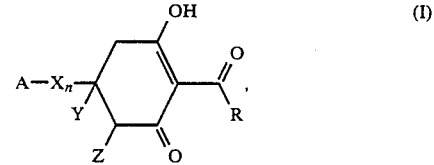

where A, X, n, Y, Z and R have the meanings given in the disclosure, or salts of these compounds, and a process for regulating plant growth.

5 Claims, No Drawings

AGENTS FOR REGULATING PLANT GROWTH

The present invention relates to agents based on cyclohexenone derivatives which regulate the growth of plants, and a process for regulating plant growth.

It is known that certain 2-acyl-3-hydroxycyclohex-2-en-1-ones have a regulatory influence on plant growth (EP-A-123 001 and EP-A-126 713). Attention is also drawn to EP-A-156 773.

We have now found novel agents for regulating plant growth which contain an effective amount of at least one cyclohexenone derivative of the formula

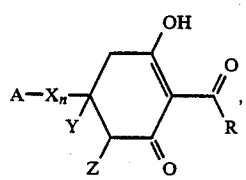

where A is alkoxycarbonyl of 2 to 5 carbon atoms, carboxyl, cyano or trifluoromethyl, X is branched or straight-chain alkylene of 1 to 7 carbon atoms or cycloalkylene of 3 to 7 carbon atoms, n is 0 or 1, with the proviso that n is not 0 when A is alkoxycarbonyl or carboxyl, Y is hydrogen or methyl, Z is hydrogen, alkoxycarbonyl of 2 to 5 carbon atoms or cyano, and R is alkyl or alkoxyalkyl, each of up to 4 carbon atoms, cyclopropyl, benzyl, phenylethyl or acyloxyalkyl, each of up to 6 carbon atoms, or one of its agriculturally acceptable salts.

In formula I, A is, for example, methoxycarbonyl, ethoxycarbonyl, propoxycarbonyl, butoxycarbonyl, carboxyl, cyano and trifluoromethyl.

X is, for instance, methylene, ethylene, trimethylene, tetramethylene, methylethylene, dimethylpentamethylene, ethyltrimethylene, 1,2-, 1,3- and 1,4-cyclohexylene, and 1,2-cyclopropylene.

Z is, for example, methoxycarbonyl, ethoxycarbonyl, cyano and hydrogen, and R is, for example, methyl, ethyl, n-propyl, isopropyl, n-butyl, sec-butyl, isobutyl, tert-butyl, cyclopropyl, benzyl, phenylethyl, methoxyethyl, acetoxymethyl and propionoxyethyl.

Examples of suitable salts of compounds of the formula I are agriculturally useful salts, such as alkali metal, especially potassium and sodium, salts, alkaline earth metal, especially calcium, magnesium and barium, salts, manganese, copper, zinc and iron salts, and ammonium, phosphonium, sulfonium and sulfoxonium salts, e.g., tetraalkylammonium salts, benzyltrialkylammonium salts, trialkylsulfonium salts and trialkylsulfoxonium salts.

DE-OS 3,440,410 discloses the use of the cyclohexenone derivatives of the formula I as intermediates for the synthesis of herbicides; their manufacture is also described.

Various synthesis routes for cyclohexenone derivatives are also given in the abovementioned European patent applications.

The synthesis of 2-butyryl-3-hydroxy-4-methoxycarbonyl-5-(4-methoxycarbonylbutyl)-cyclohex-2-en-1-one is described below by way of example.

Manufacturing Example 81 parts by weight of 3-butyryloxy-4-methoxycarbonyl-5-(4-methoxycarbonylbutyl)-cyclohex-2-en-1-one and 8 parts by weight of 4-dimethylaminopyridine were dissolved in anhydrous dichloromethane, and the solution was stirred for 48 hours at room temperature. The solution was washed with 10 wt % strength hydrochloric acid and water, and dried over sodium sulfate. The solvent was distilled off under reduced pressure to give 2-butyryl-3-hydroxy-4-methoxycarbonyl-5-(4-methoxycarbonylbutyl)-cyclohex-2-en-1-one as an oil (compound no. 4).

The compounds in the table below for which physical data are given were prepared similarly. The remaining compounds may be obtained in the same way after selection of the appropriate starting materials, and they are expected to have a biological action similar to that of the compounds investigated. Where X is an asymmetrical alkylene radical, the bond on the left in the table is attached to substituent A.

| Compound no. | A | X | n | Y | Z | R | Physical data* |
|---|---|---|---|---|---|---|---|
| 1 | $CF_3$ | 1,4-cyclohexylene | 1 | H | H | n-propyl | 0.98 (t), 3.0 (t) |
| 2 | $CF_3$ | 1,4-cyclohexylene | 1 | H | H | ethyl | |
| 3 | $COOCH_3$ | —$(CH_2)_4$— | 1 | H | $COOCH_3$ | butyl | 0.92 (t), 3.69 (s) 4.81 (t) |
| 4 | $COOCH_3$ | —$(CH_2)_4$— | 1 | H | $COOCH_3$ | n-propyl | 0.92 (t), 2.95 (t), 3.65 (s) |
| 5 | $COOCH_3$ | —$(CH_2)_4$— | 1 | H | $COOCH_3$ | ethyl | 1.17 (t), 2.35 (t), 3.83 (s) |
| 6 | $COOCH_3$ | —$(CH_2)_4$— | 1 | H | $COOCH_3$ | methyl | 2.59 (s), 3.68 (s), 3.78 (s) |
| 7 | $COOCH_3$ | —$CH(CH_3)CH_2$— | 1 | H | $COOCH_3$ | ethyl | 1.13 (t), 3.05 (q), 3.7 (s) |
| 8 | $COOCH_3$ | —$CH_2CH(CH_3)$— | 1 | H | $COOCH_3$ | methyl | |
| 9 | $COOCH_3$ | —$CH(CH_3)CH_2$— | 1 | H | $COOCH_3$ | n-propyl | 0.93 (t), 3.7 (s), 3.8 (s) |
| 10 | $COOC_2H_5$ | —$CH_2CH(CH_3)$— | 1 | H | $COOCH_3$ | n-propyl | |
| 11 | $COOn$-$C_4H_9$ | —$CH_2CH(CH_3)$— | 1 | H | $COOCH_3$ | n-propyl | |
| 12 | CN | —$CH_2CH(CH_3)$— | 1 | H | $COOCH_3$ | n-propyl | |
| 13 | $CF_3$ | —$CH(CH_3)CH_2$— | 1 | H | $COOCH_3$ | n-propyl | |
| 14 | CN | —$CH(CH_3)CH_2$— | 1 | H | $COOCH_3$ | ethyl | |
| 15 | $COOC_2H_5$ | 1,2-cyclopropylene | 1 | H | $COOCH_3$ | n-propyl | |
| 16 | $COOC_2H_5$ | 1,2-cyclopropylene | 1 | H | $COOCH_3$ | ethyl | |
| 17 | $CF_3$ | | 0 | $CH_3$ | H | n-propyl | 1.05 (t), 1.35 (s), 3.05 (t) |
| 18 | $CF_3$ | | 0 | $CH_3$ | H | ethyl | |
| 19 | $CF_3$ | | 0 | $CH_3$ | $COOCH_3$ | n-propyl | 1.4 (s), 1.65 (q), 3.8 (s) |
| 20 | $CF_3$ | | 0 | $CH_3$ | $COOCH_3$ | ethyl | |

-continued

| No. | | | | | | | |
|---|---|---|---|---|---|---|---|
| 21 | COOH | | 0 | H | COOCH₃ | ethyl | |
| 22 | COOH | | 0 | H | COOCH₃ | n-propyl | |
| 23 | —COOCH₃ | —CH₂CH(CH₃)(CH₂)₃— | 1 | H | COOCH₃ | n-propyl | 0.9 (t), 3.6 (s), 3.7 (s) |
| 24 | —COOCH₃ | —CH₂CH(CH₃)(CH₂)₃— | 1 | H | COOCH₃ | ethyl | |
| 25 | —COOCH₃ | 1,2-cyclopropylene | 1 | H | H | methyl | |
| 26 | —COOCH₃ | 1,2-cyclopropylene | 1 | H | H | ethyl | |
| 27 | —COOCH₃ | 1,2-cyclopropylene | 1 | H | H | n-propyl | |
| 28 | —COO-n-C₄H₉ | 1,2-cyclopropylene | 1 | H | H | methyl | |
| 29 | —COO-n-C₄H₉ | 1,2-cyclopropylene | 1 | H | H | ethyl | |
| 30 | —COO-n-C₄H₉ | 1,2-cyclopropylene | 1 | H | H | n-propyl | |
| 31 | —COO-tert-C₄H₉ | 1,2-cyclopropylene | 1 | H | H | methyl | |
| 32 | —COO-tert-C₄H₉ | 1,2-cyclopropylene | 1 | H | H | ethyl | |
| 33 | —COO-tert-C₄H₉ | 1,2-cyclopropylene | 1 | H | H | n-propyl | |
| 34 | —COOH | 1,2-cyclopropylene | 1 | H | H | methyl | |
| 35 | —COOH | 1,2-cyclopropylene | 1 | H | H | ethyl | |
| 36 | —COOH | 1,2-cyclopropylene | 1 | H | H | n-propyl | 1.0 (t), 3.0 (t) |
| 37 | —CN | 1,2-cyclopropylene | 1 | H | H | methyl | |
| 38 | —CN | 1,2-cyclopropylene | 1 | H | H | ethyl | |
| 39 | —CN | 1,2-cyclopropylene | 1 | H | H | n-propyl | |
| 40 | —COOCH₃ | 1,2-cyclohexylene | 1 | H | H | methyl | |
| 41 | —COOCH₃ | 1,2-cyclohexylene | 1 | H | H | ethyl | |
| 42 | —COOCH₃ | 1,2-cyclohexylene | 1 | H | H | n-propyl | |
| 43 | —COO-n-C₄H₉ | 1,2-cyclohexylene | 1 | H | H | methyl | |
| 44 | —COO-n-C₄H₉ | 1,2-cyclohexylene | 1 | H | H | ethyl | |
| 45 | —COO-n-C₄H₉ | 1,2-cyclohexylene | 1 | H | H | n-propyl | |
| 46 | —COO-tert-C₄H₉ | 1,2-cyclohexylene | 1 | H | H | methyl | |
| 47 | —COO-tert-C₄H₉ | 1,2-cyclohexylene | 1 | H | H | ethyl | |
| 48 | —COO-tert-C₄H₉ | 1,2-cyclohexylene | 1 | H | H | n-propyl | |
| 49 | —COOH | 1,2-cyclohexylene | 1 | H | H | methyl | |
| 50 | —COOH | 1,2-cyclohexylene | 1 | H | H | ethyl | |
| 51 | —COOH | 1,2-cyclohexylene | 1 | H | H | n-propyl | |
| 52 | —CN | 1,2-cyclohexylene | 1 | H | H | methyl | |
| 53 | —CN | 1,2-cyclohexylene | 1 | H | H | ethyl | |
| 54 | —CN | 1,2-cyclohexylene | 1 | H | H | n-propyl | |
| 55 | —COOCH₃ | 1,3-cyclohexylene | 1 | H | H | methyl | |
| 56 | —COOCH₃ | 1,3-cyclohexylene | 1 | H | H | ethyl | |
| 57 | —COOCH₃ | 1,3-cyclohexylene | 1 | H | H | n-propyl | |
| 58 | —COO-n-C₄H₉ | 1,3-cyclohexylene | 1 | H | H | methyl | |
| 59 | —COO-n-C₄H₉ | 1,3-cyclohexylene | 1 | H | H | ethyl | |
| 60 | —COO-n-C₄H₉ | 1,3-cyclohexylene | 1 | H | H | n-propyl | |
| 61 | —COO-tert-C₄H₉ | 1,3-cyclohexylene | 1 | H | H | methyl | |
| 62 | —COO-tert-C₄H₉ | 1,3-cyclohexylene | 1 | H | H | ethyl | |
| 63 | —COO-tert-C₄H₉ | 1,3-cyclohexylene | 1 | H | H | n-propyl | |
| 64 | —COOH | 1,3-cyclohexylene | 1 | H | H | methyl | |
| 65 | —COOH | 1,3-cyclohexylene | 1 | H | H | ethyl | |
| 66 | —COOH | 1,3-cyclohexylene | 1 | H | H | n-propyl | |
| 67 | —CN | 1,3-cyclohexylene | 1 | H | H | methyl | |
| 68 | —CN | 1,3-cyclohexylene | 1 | H | H | ethyl | |
| 69 | —CN | 1,3-cyclohexylene | 1 | H | H | n-propyl | |
| 70 | —COOCH₃ | 1,4-cyclohexylene | 1 | H | H | methyl | |
| 71 | —COOCH₃ | 1,4-cyclohexylene | 1 | H | H | ethyl | |
| 72 | —COOCH₃ | 1,4-cyclohexylene | 1 | H | H | n-propyl | |
| 73 | —COO-n-C₄H₉ | 1,4-cyclohexylene | 1 | H | H | methyl | |
| 74 | —COO-n-C₄H₉ | 1,4-cyclohexylene | 1 | H | H | ethyl | |
| 75 | —COO-n-C₄H₉ | 1,4-cyclohexylene | 1 | H | H | n-propyl | |
| 76 | —COO-tert-C₄H₉ | 1,4-cyclohexylene | 1 | H | H | methyl | |
| 77 | —COO-tert-C₄H₉ | 1,4-cyclohexylene | 1 | H | H | ethyl | |
| 78 | —COO-tert-C₄H₉ | 1,4-cyclohexylene | 1 | H | H | n-propyl | |
| 79 | —COOH | 1,4-cyclohexylene | 1 | H | H | methyl | |
| 80 | —COOH | 1,4-cyclohexylene | 1 | H | H | ethyl | |
| 81 | —COOH | 1,4-cyclohexylene | 1 | H | H | n-propyl | |
| 82 | —CN | 1,4-cyclohexylene | 1 | H | H | methyl | |
| 83 | —CN | 1,4-cyclohexylene | 1 | H | H | ethyl | |
| 84 | —CN | 1,4-cyclohexylene | 1 | H | H | n-propyl | |
| 85 | —COOCH₃ | methylene | 1 | H | H | methyl | |
| 86 | —COOCH₃ | methylene | 1 | H | H | ethyl | |
| 87 | —COOCH₃ | methylene | 1 | H | H | n-propyl | |
| 88 | —COO-n-C₄H₉ | methylene | 1 | H | H | methyl | |
| 89 | —COO-n-C₄H₉ | methylene | 1 | H | H | ethyl | |
| 90 | —COO-n-C₄H₉ | methylene | 1 | H | H | n-propyl | |
| 91 | —COO-tert-C₄H₉ | methylene | 1 | H | H | methyl | |
| 92 | —COO-tert-C₄H₉ | methylene | 1 | H | H | ethyl | |
| 93 | —COO-tert-C₄H₉ | methylene | 1 | H | H | n-propyl | |
| 94 | —COOH | methylene | 1 | H | H | methyl | |
| 95 | —COOH | methylene | 1 | H | H | ethyl | |
| 96 | —COOH | methylene | 1 | H | H | n-propyl | |
| 97 | —CN | methylene | 1 | H | H | methyl | |
| 98 | —CN | methylene | 1 | H | H | ethyl | |
| 99 | —CN | methylene | 1 | H | H | n-propyl | |
| 100 | —COOCH₃ | ethylene | 1 | H | H | methyl | |
| 101 | —COOCH₃ | ethylene | 1 | H | H | ethyl | |

-continued

| No. | | | | | | | |
|---|---|---|---|---|---|---|---|
| 102 | —COOCH₃ | ethylene | 1 | H | H | n-propyl | |
| 103 | —COO-n-C₄H₉ | ethylene | 1 | H | H | methyl | |
| 104 | —COO-n-C₄H₉ | ethylene | 1 | H | H | ethyl | |
| 105 | —COO-n-C₄H₉ | ethylene | 1 | H | H | n-propyl | |
| 106 | —COO-tert-C₄H₉ | ethylene | 1 | H | H | methyl | |
| 107 | —COO-tert-C₄H₉ | ethylene | 1 | H | H | ethyl | |
| 108 | —COO-tert-C₄H₉ | ethylene | 1 | H | H | n-propyl | |
| 109 | —COOH | ethylene | 1 | H | H | methyl | |
| 110 | —COOH | ethylene | 1 | H | H | ethyl | |
| 111 | —COOH | ethylene | 1 | H | H | n-propyl | |
| 112 | —CN | ethylene | 1 | H | H | methyl | |
| 113 | —CN | ethylene | 1 | H | H | ethyl | |
| 114 | —CN | ethylene | 1 | H | H | n-propyl | |
| 115 | —COOCH₃ | trimethylene | 1 | H | H | methyl | |
| 116 | —COOCH₃ | trimethylene | 1 | H | H | ethylene | |
| 117 | —COOCH₃ | trimethylene | 1 | H | H | n-propyl | 0.95 (t), 3.01 (t) 3.69 (s) |
| 118 | —COO-n-C₄H₉ | trimethylene | 1 | H | H | methyl | |
| 119 | —COO-n-C₄H₉ | trimethylene | 1 | H | H | ethyl | |
| 120 | —COO-n-C₄H₉ | trimethylene | 1 | H | H | n-propyl | |
| 121 | —COO-tert-C₄H₉ | trimethylene | 1 | H | H | methyl | |
| 122 | —COO-tert-C₄H₉ | trimethylene | 1 | H | H | ethyl | |
| 123 | —COO-tert-C₄H₉ | trimethylene | 1 | H | H | n-propyl | |
| 124 | —COOH | trimethylene | 1 | H | H | methyl | |
| 125 | —COOH | trimethylene | 1 | H | H | ethyl | |
| 126 | —COOH | trimethylene | 1 | H | H | n-propyl | 0.89 (t), 2.93 (t), 12.0 (s) |
| 127 | —CN | trimethylene | 1 | H | H | methyl | |
| 128 | —CN | trimethylene | 1 | H | H | ethyl | |
| 129 | —CN | trimethylene | 1 | H | H | n-propyl | |
| 130 | —COOCH₃ | tetramethylene | 1 | H | H | methyl | 1.42 (m), 2.63 (s), 3.70 (s) |
| 131 | —COOCH₃ | tetramethylene | 1 | H | H | ethyl | 1.13 (t), 3.05 (q), 3.66 (s) |
| 132 | —COOCH₃ | tetramethylene | 1 | H | H | n-propyl | 1.02 (t), 3.00 (t), 3.69 (s) |
| 133 | —COO-n-C₄H₉ | tetramethylene | 1 | H | H | methyl | 0.93 (t), 2.61 (s), 4.07 (t) |
| 134 | —COO-n-C₄H₉ | tetramethylene | 1 | H | H | ethyl | 0.93 (t), 3.05 (q), 4.07 (t) |
| 135 | —COO-n-C₄H₉ | tetramethylene | 1 | H | H | n-propyl | 2.32 (t), 3.02 (t), 4.10 (t) |
| 136 | —COO-tert-C₄H₉ | tetramethylene | 1 | H | H | methyl | |
| 137 | —COO-tert-C₄H₉ | tetramethylene | 1 | H | H | ethyl | |
| 138 | —COO-tert-C₄H₉ | tetramethylene | 1 | H | H | n-propyl | |
| 139 | —COOH | tetramethylene | 1 | H | H | methyl | 1.40 (m), 2.30 (t), 2.59 (s) |
| 140 | —COOH | tetramethylene | 1 | H | H | ethyl | 97–98 |
| 141 | —COOH | tetramethylene | 1 | H | H | n-propyl | 64 |
| 142 | —CN | tetramethylene | 1 | H | H | methyl | |
| 143 | —CN | tetramethylene | 1 | H | H | ethyl | |
| 144 | —CN | tetramethylene | 1 | H | H | n-propyl | |
| 145 | —COOCH₃ | —CH(CH₃)(CH₂)₃— | 1 | H | H | methyl | |
| 146 | —COOCH₃ | —CH(CH₃)(CH₂)₃— | 1 | H | H | ethyl | |
| 147 | —COOCH₃ | —CH(CH₃)(CH₂)₃— | 1 | H | H | n-propyl | |
| 148 | —COO-n-C₄H₉ | —CH(CH₃)(CH₂)₃— | 1 | H | H | methyl | |
| 149 | —COO-n-C₄H₉ | —CH(CH₃)(CH₂)₃— | 1 | H | H | ethyl | |
| 150 | —COO-n-C₄H₉ | —CH(CH₃)(CH₂)₃— | 1 | H | H | n-propyl | |
| 151 | —COO-tert-C₄H₉ | —CH(CH₃)(CH₂)₃— | 1 | H | H | methyl | |
| 152 | —COO-tert-C₄H₉ | —CH(CH₃)(CH₂)₃— | 1 | H | H | ethyl | |
| 153 | —COO-tert-C₄H₉ | —CH(CH₃)(CH₂)₃— | 1 | H | H | n-propyl | |
| 154 | —COOH | —CH(CH₃)(CH₂)₃— | 1 | H | H | methyl | |
| 155 | —COOH | —CH(CH₃)(CH₂)₃— | 1 | H | H | ethyl | |
| 156 | —COOH | —CH(CH₃)(CH₂)₃— | 1 | H | H | n-propyl | |
| 157 | —CN | —CH(CH₃)(CH₂)₃— | 1 | H | H | methyl | |
| 158 | —CN | —CH(CH₃)(CH₂)₃— | 1 | H | H | ethyl | |
| 159 | —CN | —CH(CH₃)(CH₂)₃— | 1 | H | H | n-propyl | |
| 160 | —COOCH₃ | —CH(CH₃)CH₂— | 1 | H | H | methyl | |
| 161 | —COOCH₃ | —CH(CH₃)CH₂— | 1 | H | H | ethyl | |
| 162 | —COOCH₃ | —CH(CH₃)CH₂— | 1 | H | H | n-propyl | |
| 163 | —COO-n-C₄H₉ | —CH(CH₃)CH₂— | 1 | H | H | methyl | |
| 164 | —COO-n-C₄H₉ | —CH(CH₃)CH₂— | 1 | H | H | ethyl | |
| 165 | —COO-n-C₄H₉ | —CH(CH₃)CH₂— | 1 | H | H | n-propyl | |
| 166 | —COO-tert-C₄H₉ | —CH(CH₃)CH₂— | 1 | H | H | methyl | |
| 167 | —COO-tert-C₄H₉ | —CH(CH₃)CH₂— | 1 | H | H | ethyl | |
| 168 | —COO-tert-C₄H₉ | —CH(CH₃)CH₂— | 1 | H | H | n-propyl | |
| 169 | —COOH | —CH(CH₃)CH₂— | 1 | H | H | methyl | |
| 170 | —COOH | —CH(CH₃)CH₂— | 1 | H | H | ethyl | 1.3 (m), 2.5 (m), 3.1 (q) |
| 171 | —COOH | —CH(CH₃)CH₂— | 1 | H | H | n-propyl | 1.0 (t), 3.0 (q) |
| 172 | —CN | —CH(CH₃)CH₂— | 1 | H | H | methyl | |
| 173 | —CN | —CH(CH₃)CH₂— | 1 | H | H | ethyl | |

-continued

| | | | | | | | |
|---|---|---|---|---|---|---|---|
| 174 | —CN | —CH(CH₃)CH₂— | 1 | H | H | n-propyl | |
| 175 | —COOCH₃ | —CH₂CH(CH₃)— | 1 | H | H | Methyl | |
| 176 | —COOCH₃ | —CH₂CH(CH₃)— | 1 | H | H | ethyl | |
| 177 | —COOCH₃ | —CH₂CH(CH₃)— | 1 | H | H | n-propyl | |
| 178 | —COO-n-C₄H₉ | —CH₂CH(CH₃)— | 1 | H | H | methyl | |
| 179 | —COO-n-C₄H₉ | —CH₂CH(CH₃)— | 1 | H | H | ethyl | |
| 180 | —COO-n-C₄H₉ | —CH₂CH(CH₃)— | 1 | H | H | n-propyl | |
| 181 | —COO-tert-C₄H₉ | —CH₂CH(CH₃)— | 1 | H | H | methyl | |
| 182 | —COO-tert-C₄H₉ | —CH₂CH(CH₃)— | 1 | H | H | ethyl | |
| 183 | —COO-tert-C₄H₉ | —CH₂CH(CH₃)— | 1 | H | H | n-propyl | |
| 184 | —COOH | —CH₂CH(CH₃)— | 1 | H | H | methyl | |
| 185 | —COOH | —CH₂CH(CH₃)— | 1 | H | H | ethyl | |
| 186 | —COOH | —CH₂CH(CH₃)— | 1 | H | H | n-propyl | |
| 187 | —CN | —CH₂CH(CH₃-)— | 1 | H | H | methyl | |
| 188 | —CN | —CH₂CH(CH₃)— | 1 | H | H | ethyl | |
| 189 | —CN | —CH₂CH(CH₃)— | 1 | H | H | n-propyl | |
| 190 | —COOCH₃ | —(CH₂)₃CH(CH₃)CH₂— | 1 | H | H | methyl | |
| 191 | —COOCH₃ | —(CH₂)₃CH(CH₃)CH₂— | 1 | H | H | ethyl | |
| 192 | —COOCH₃ | —(CH₂)₃CH(CH₃)CH₂— | 1 | H | H | n-propyl | 1.0 (t), 3.1 (t), 3.7 (s) |
| 193 | —COO-n-C₄H₉ | —(CH₂)₃CH(CH₃)CH₂— | 1 | H | H | methyl | |
| 194 | —COO-n-C₄H₉ | —(CH₂)₃CH(CH₃)CH₂— | 1 | H | H | ethyl | |
| 195 | —COO-n-C₄H₉ | —(CH₂)₃CH(CH₃)CH₂— | 1 | H | H | n-propyl | |
| 196 | —COO-tert-C₄H₉ | —(CH₂)₃CH(CH₃)CH₂— | 1 | H | H | methyl | |
| 197 | —COO-tert-C₄H₉ | —(CH₂)₃CH(CH₃)CH₂— | 1 | H | H | ethyl | |
| 198 | —COO-tert-C₄H₉ | —(CH₂)₃CH(CH₃)CH₂— | 1 | H | H | n-propyl | |
| 199 | —COOH | —(CH₂)₃CH(CH₃)CH₂— | 1 | H | H | methyl | |
| 200 | —COOH | —(CH₂)₃CH(CH₃)CH₂— | 1 | H | H | ethyl | |
| 201 | —COOH | —(CH₂)₃CH(CH₃)CH₂— | 1 | H | H | n-propyl | |
| 202 | —CN | —(CH₂)₃CH(CH₃)CH₂— | 1 | H | H | methyl | |
| 203 | —CN | —(CH₂)₃CH(CH₃)CH₂— | 1 | H | H | ethyl | |
| 204 | —CN | —(CH₂)₃CH(CH₃)CH₂— | 1 | H | H | n-propyl | |
| 205 | —COOCH₃ | —CH(CH₃)(CH₂)₂CH(CH₃)CH₂— | 1 | H | H | methyl | |
| 206 | —COOCH₃ | —CH(CH₃)(CH₂)₂CH(CH₃)CH₂— | 1 | H | H | ethyl | |
| 207 | —COOCH₃ | —CH(CH₃)(CH₂)₂CH(CH₃)CH₂— | 1 | H | H | n-propyl | |
| 208 | —COO-n-C₄H₉ | —CH(CH₃)(CH₂)₂CH(CH₃)CH₂— | 1 | H | H | methyl | |
| 209 | —COO-n-C₄H₉ | —CH(CH₃)(CH₂)₂CH(CH₃)CH₂— | 1 | H | H | ethyl | |
| 210 | —COO-n-C₄H₉ | —CH(CH₃)(CH₂)₂CH(CH₃)CH₂— | 1 | H | H | n-propyl | |
| 211 | —COO-tert-C₄H₉ | —CH(CH₃)(CH₂)₂CH(CH₃)CH₂— | 1 | H | H | methyl | |
| 212 | —COO-tert-C₄H₉ | —CH(CH₃)(CH₂)₂CH(CH₃)CH₂ | 1 | H | H | ethyl | |
| 213 | —COO-tert-C₄H₉ | —CH(CH₃)(CH₂)₂CH(CH₃)CH₂ | 1 | H | H | n-propyl | |
| 214 | —COOH | —CH(CH₃)(CH₂)₂CH(CH₃)CH₂— | 1 | H | H | methyl | |
| 215 | —COOH | —CH(CH₃)(CH₂)₂CH(CH₃)CH₂— | 1 | H | H | ethyl | |
| 216 | —COOH | —CH(CH₃)(CH₂)₂CH(CH₃)CH₂— | 1 | H | H | n-propyl | |
| 217 | —CN | —CH(CH₃)(CH₂)₂CH(CH₃)CH₂— | 1 | H | H | methyl | |
| 218 | —CN | —CH(CH₃)(CH₂)₂CH(CH₃)CH₂— | 1 | H | H | ethyl | |
| 219 | —CN | —CH(CH₃)(CH₂)₂CH(CH₃)CH₂— | 1 | H | H | n-propyl | |
| 220 | —COOCH₃ | —(CH₂)₂CH(C₂H₅)— | 1 | H | H | methyl | |
| 221 | —COOCH₃ | —(CH₂)₂CH(C₂H₅)— | 1 | H | H | ethyl | 0.91 (t), 3.06 (q), 3.70 (s) |
| 222 | —COOCH₃ | —(CH₂)₂CH(C₂H₅)— | 1 | H | H | n-propyl | |
| 223 | —COO-n-C₄H₉ | —(CH₂)₂CH(C₂H₅)— | 1 | H | H | methyl | |
| 224 | —COO-n-C₄H₉ | —(CH₂)₂CH(C₂H₅)— | 1 | H | H | ethyl | |
| 225 | —COO-n-C₄H₉ | —(CH₂)₂CH(C₂H₅)— | 1 | H | H | n-propyl | |
| 226 | —COO-tert-C₄H₉ | —(CH₂)₂CH(C₂H₅)— | 1 | H | H | methyl | |
| 227 | —COO-tert-C₄H₉ | —(CH₂)₂CH(C₂H₅)— | 1 | H | H | ethyl | |
| 228 | —COO-tert-C₄H₉ | —(CH₂)₂CH(C₂H₅)— | 1 | H | H | n-propyl | |
| 229 | —COOH | —(CH₂)₂CH(C₂H₅)— | 1 | H | H | methyl | |
| 230 | —COOH | —(CH₂)₂CH(C₂H₅)— | 1 | H | H | ethyl | 0.9 (t), 1.1 (t), 3.1 (q) |
| 231 | —COOH | —(CH₂)₂CH(C₂H₅)— | 1 | H | H | n-propyl | |
| 232 | —CN | —(CH₂)₂CH(C₂H₅)— | 1 | H | H | methyl | |
| 233 | —CN | —(CH₂)₂CH(C₂H₅)— | 1 | H | H | ethyl | |
| 234 | —CN | —(CH₂)₂CH(C₂H₅)— | 1 | H | H | n-propyl | |
| 235 | —COOH | —CH(CH₃)(CH₂)₂CH(CH₃)CH₂— | 1 | COOCH₃ | H | n-propyl | |
| 236 | —CF₃ | 1,3-cyclohexylene | 1 | H | H | n-propyl | 0.99 (t), 3.02 (t) |
| 237 | —CN | —CH(CH₃)— | 1 | H | H | n-propyl | |
| 238 | COO-tert-C₄H₉ | —CH(CH₃)— | 1 | H | H | n-propyl | 0.95 (t), 1.4 (s), 3.0 (t) |
| 239 | —COOCH₃ | —CH(CH₃)(CH₂)₂CH(CH₃)CH₂ | 1 | H | H | n-propyl | 1.4920 |
| 240 | —COOH | —CH(CH₃)— | 1 | H | H | ethyl | 2.97 (q), 12.35 (s), 17.90 (s) |
| 241 | —COO-n-C₄H₉ | —CH(CH₃)— | 1 | H | H | ethyl | 0.95 (t), 3.07 (q), 4.11 (t) |
| 242 | —COOCH₃ | —CH(CH₃)— | 1 | H | H | ethyl | 1.13 (t), 1.21 (d), 3.72 (s) |
| 243 | —COOCH₃ | —CH(CH₃)— | 1 | H | COOCH₃ | ethyl | 3.03 (m), 3.71 (s), 3.82 (s) |
| 244 | —COOH | —C(CH₃)₂— | 1 | H | H | propyl | 0.98 (t), 1.25 (s), 3.01 (t) |
| 245 | —COOCH₃ | —C(CH₃)₂— | 1 | H | H | propyl | 0.98 (t), 1.22 (s), 3.72 (s) |

-continued

| | | | | | | | |
|---|---|---|---|---|---|---|---|
| 246 | —COOH | —(CH$_2$)$_2$CH(CH$_3$)— | 1 | H | H | ethyl | 0.96 (d), 1.14 (t), 3.05 (q) |
| 247 | —COOCH$_3$ | —(CH$_2$)$_2$CH(CH$_3$)— | 1 | H | H | ethyl | 0.91 (d), 3.03 (q), 3.68 (s) |
| 248 | —COOCH$_3$ | —(CH$_2$)$_2$CH(CH$_3$)— | 1 | H | H | propyl | 0.95 (m), 3.00 (t), 3.70 (s) |
| 249 | —COOCH$_3$ | —(CH$_2$)$_2$CH(CH$_3$)— | 1 | H | COOCH$_3$ | propyl | 0.94 (m), 2.98 (t), 3.68 (s) |
| 250 | —COOH | —(CH$_2$)$_4$— | 1 | H | H | butyl | 0.92 (t), 2.37 (t), 3.02 (t) |
| 251 | —COO-n-C$_4$H$_9$ | —(CH$_2$)$_4$— | 1 | H | H | butyl | 0.95 (m), 3.01 (t), 4.09 (t) |
| 252 | —COOCH$_3$ | —(CH$_2$)$_4$— | 1 | H | H | butyl | 0.95 (t), 3.02 (t), 3.72 (s) |
| 253 | —COOH | —(CH$_2$)$_2$CH(CH$_3$)CH$_2$— | 1 | H | H | ethyl | 0.89 (d), 1.17 (t), 3.04 (q) |
| 254 | —COOH | —(CH$_2$)$_2$CH(CH$_3$)CH$_2$— | 1 | H | H | butyl | 0.92 (m), 2.32 (t), 3.01 (t) |
| 255 | —COOCH$_3$ | —(CH$_2$)$_2$CH(CH$_3$)CH$_2$— | 1 | H | H | ethyl | 0.90 (d), 3.05 (q), 3.67 (s) |
| 256 | —COOCH$_3$ | —(CH$_2$)$_2$CH(CH$_3$)CH$_2$— | 1 | H | H | butyl | 0.90 (m), 3.02 (t), 3.68 (s) |
| 257 | —COO-n-C$_4$H$_9$ | —(CH$_2$)$_2$CH(CH$_3$)CH$_2$— | 1 | H | H | methyl | 0.90 (m), 2.62 (s), 4.07 (t) |
| 258 | —COOH | —(CH$_2$)$_2$CH(CH$_3$)CH$_2$— | 1 | H | H | methyl | 0.92 (d), 2.33 (t), 2.62 (s) |
| 259 | —COOH | —(CH$_2$)$_2$CH(CH$_3$)CH$_2$— | 1 | H | H | propyl | 0.91 (d), 2.33 (t), 3.02 (t) |
| 260 | —COOCH$_3$ | —(CH$_2$)$_2$CH(CH$_3$)CH$_2$— | 1 | H | H | methyl | 0.88 (d), 2.61 (s), 3.68 (s) |
| 261 | —COOCH$_3$ | —(CH$_2$)$_2$CH(CH$_3$)CH$_2$— | 1 | H | H | propyl | 0.89 (d), 3.01 (t), 3.69 (s) |
| 262 | —COO-n-C$_4$H$_9$ | —(CH$_2$)$_2$CH(CH$_3$)CH$_2$— | 1 | H | H | ethyl | 1.18 (t), 3.07 (q), 4.08 (t) |
| 263 | —COO-n-C$_4$H$_9$ | —(CH$_2$)$_2$CH(CH$_3$)CH$_2$— | 1 | H | H | butyl | 2.29 (t), 3.03 (t), 4.08 (t) |
| 264 | —COOCH$_3$ | —(CH$_2$)$_2$CH(CH$_3$)CH$_2$— | 1 | H | COOCH$_3$ | propyl | 0.90 (m), 3.70 (s), 3.79 (s) |
| 265 | —COOCH$_3$ | —(CH$_2$)$_2$CH(CH$_3$)CH$_2$— | 1 | H | COOCH$_3$ | methyl | 2.62 (s), 3.67 (s), 3.78 (s) |
| 266 | —COOCH$_3$ | —(CH$_2$)$_2$CH(CH$_3$)CH$_2$— | 1 | H | COOCH$_3$ | ethyl | 1.12 (t), 3.04 (q), 3.67 (s) |
| 267 | —COOCH$_3$ | —(CH$_2$)$_2$CH(CH$_3$)CH$_2$— | 1 | H | COOCH$_3$ | butyl | 0.92 (m), 3.68 (s), 3.79 (s) |
| 268 | —COO-n-C$_4$H$_9$ | —(CH$_2$)$_2$CH(CH$_3$)CH$_2$— | 1 | H | H | propyl | 2.28 (t), 3.01 (t), 4.07 (t) |

| Compound no. | Salt of compound no. | Cation(s) |
|---|---|---|
| 269 | 141 | 2 Na$^+$ |
| 270 | 141 | Ca$^{2+}$ |
| 271 | 139 | 2 Na$^+$ |
| 269 | 141 | 2 Na$^+$ |
| 272 | 258 | Ca$^{2+}$ |
| 273 | 258 | 2 Na$^+$ |
| 274 | 140 | 2 Na$^+$ |
| 275 | 139 | Ca$^{2+}$ |
| 276 | 250 | 2 Na$^+$ |
| 277 | 253 | Ca$^{2+}$ |
| 278 | 253 | 2 Na$^+$ |
| 279 | 140 | 2 benzyltrimethylammonium |
| 280 | 258 | 2 benzyltrimethylammonium |
| 281 | 259 | 2 Na$^+$ |
| 282 | 254 | 2 Na$^+$ |
| 283 | 253 | 2 benzyltrimethylammonium |
| 284 | 139 | 2 benzyltrimethylammonium |

*Physical data given are melting point (°C.), refractive index and $^1$H-NMR signals (ppm), the abbreviations having the following meanings: s = singlet, d = doublet, t = triplet, q = quartet, m = multiplet The cyclohexenone derivatives of the formula I may have a variety of influences on practically all plant development stages, and are therefore used as growth regulators.

The active ingredients to be used in accordance with the invention may be applied to the crop either by treating the seed, treating the soil (i.e., via the roots), or—the method particularly preferred—by spraying the leaves.

Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.01 to 12 kg/ha, preferably from 0.25 to 3 kg/ha, are generally considered to be sufficient.

The agents according to the invention may be applied in the usual formulation forms, e.g. solutions, emulsions, suspensions, powders, dusts, pastes or granules.

The agents according to the invention many, in these application forms, also be mixed and applied with other active ingredients, e.g., herbicides, insecticides, other growth regulators, fungicides and fertilizers. When mixed with other growth regulators, synergistic effects also occur; i.e., the action of the combination product is greater than the effect of the individual components added together.

To determine the growth-regulating properties of the compounds, a culture substrate provided with sufficient nutrients was filled into plastic pots 12.5 cm in diameter, and test plants were grown therein.

In the postemergence application method, the candidate compounds were sprayed onto the plants as aqueous formulations. In other experiments, aqueous formulations were applied to the substrate before emergence of the plants. The growth-regulating action observed was confirmed at the end of the experiment by measuring the growth height. The figures obtained were compared with those for untreated plants.

For example, compound no. 140 exhibits clear growth-retarding properties, inter alia in wheat, barley and rice.

Not only was growth height reduced—the leaves also took on a more intense color. The increased chlorophyll content is indicative of a higher rate of photosynthesis, making for bigger yields.

The bio-regulatory properties of the compounds according to the invention were investigated in various series of tests. The compounds used for comparison purposes were:

| | |
|---|---|
| A | Chlormequat chloride |
| B | Ex. no. 13 from EP 0 123 001 A1 |
| C | Ex. no. 15 from EP 0 123 001 A1 |
| D | Daminozid |
| E | Mepiquat chloride |

1. Test with seedlings under greenhouse conditions

To determine the growth-regulating properties of the candidate compounds, test plants were grown in soil provided with sufficient nutrients in plastic pots (approx. 12.5 cm in diameter; volume: approx. 500 ml).

The compounds were sprayed as aqueous formulations onto the substrate either on the day of sowing (pre-emergence) or after germination (postemergence). The growth-regulating action observed was confirmed at the end of the experiment by measuring the growth height. The figures obtained were compared with those for untreated plants.

Not only was growth height reduced—the leaves also took on a more intense color. The increased chlorophyll content is indicative of a higher rate of photosynthesis, making for bigger yields.

Experiment 1

Spring barley, Aramir variety
Preemergence (soil) treatment

In this experiment, compounds nos. 130, 131, 134 and 140 had a much stronger influence on growth height than comparative compounds A, B and C, without damaging the seedlings.

Experiment 2

Rice, Nihonbare variety
Postemergence soil treatment

Compound no. 140 proved, in various concentrations, to be much more effective than A or C; A (Cycocel) was completely ineffective.

2. Reduction in stem length and yield improvement in rice 10 rice plants of the Girona variety were cultivated in plastic pots according to Kich-Brauckmann under greenhouse conditions. 4.5 g of a peat substrate provided with sufficient mineral nutrient salts was employed per vessel. The substrate was flooded with water.

When the plants had grown to a height of 21 cm, the candidate compounds were poured onto the substrate as aqueous formulations. This application method is substantially equivalent to the soil-drenching method frequently employed for rice.

Compound 140 reduced the height of the rice plants to a greater degree than comparative compound C. It is to be expected that the tendency of plants to lodge will be less under the influence of compound 140 than under that of C. Further, a significantly improved yield and a more favorable harvest index (ratio of grain yield to straw mass) were achieved with compound 140— at least at an application rate of 5 mg of active ingredient per vessel. Comparative compound C reduced yield and had a less favorable harvest index.

3. Rice seedling test

Young rice seedlings ("Girona" variety) were cultivated in nutrient solutions containing different concentrations of the active ingredients. After 6 days at 25° C. in continuous light, the active ingredient concentration was determined which reduced lengthwise growth of the second leaf-sheath by 50% ($=KI_{50}$).

(For details, see W. Rademacher and J. Jung, Z. Acher- und Pflanzenbau, 150, 363"371, 1981).

The figures obtained show that compounds 6, 130, 131, 132, 133, 134, 135, 140, 141, 251, 269, 271, 274, 275, 279, 280 and 284 according to the invention achieve the same effect—at much lower application rates—than comparative compounds A, D and E.

We claim:

1. A composition for regulating plant growth containing a solid or liquid carrier and a plant growth regulating amount of at least one cyclohexenone derivative of the formula

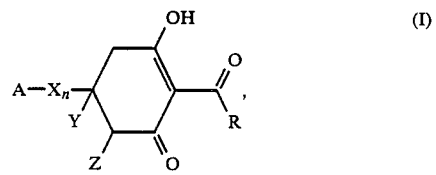

where A is alkoxycarbonyl of 2 to 5 carbon atoms, carboxyl, cyano or trifluoromethyl, X is branched or straight-chain alkylene of 4 to 7 carbon atoms whereby A and the cyclohexene ring are separated by at least 4 carbon atoms, or cycloalkylene of 3 to 7 carbon atoms, n is 0 or 1, with the proviso that n is not 0 when A is alkoxycarbonyl, cyano or carboxyl, Y is hydrogen or methyl, Z is hydrogen, alkoxycarbonyl of 2 to 5 carbon atoms or cyano, and R is alkyl or alkoxyalkyl, each of up to 4 carbon atoms, cyclopropyl, benzyl or phenylethyl, or one of its agriculturally acceptable salts.

2. A process for regulating plant growth, wherein at least one cyclohexenone derivative of the formula I as set forth in claim 1 is allowed to act on plants or their biotope.

3. A composition as defined in claim 1, wherein R is alkyl of 1 to 4 carbon atoms.

4. A composition as defined in claim 1, wherein n is 1 and X is $C_4$–$C_7$-alkylene.

5. A process for regulating plant growth, wherein at least one cyclohexenone derivative as set forth in claim 4 is allowed to act on plants or their biotope.

* * * * *